United States Patent [19]
Minagawa, deceased et al.

[11] 3,973,574
[45] Aug. 10, 1976

[54] WAVING AND STRAIGHTENING HAIR BY PRODUCING METAL CHELATES IN THE KERATIN OF THE HAIR

[75] Inventors: Toyosaku Minagawa, deceased, late of Tokyo, Japan, by Motoi Minagawa, administrator; Yuzi Hazaka, Fujisawa; Fumio Umezawa, Tokyo, both of Japan

[73] Assignee: Fumio Umezawa, Tokyo, Japan

[22] Filed: Dec. 7, 1973

[21] Appl. No.: 422,710

Related U.S. Application Data

[63] Continuation of Ser. No. 100,539, Dec. 21, 1970, abandoned, which is a continuation-in-part of Ser. No. 596,391, Dec. 17, 1966, abandoned.

[30] Foreign Application Priority Data

| Nov. 25, 1965 | Japan | 40-71974 |
| Dec. 21, 1965 | Japan | 40-79172 |
| Jan. 11, 1966 | Japan | 41-1455 |
| May 4, 1966 | Japan | 41-28168 |
| Oct. 3, 1966 | Japan | 41-65070 |

[52] U.S. Cl. ............................... 132/7; 8/10; 8/10.1; 8/127.51; 424/71
[51] Int. Cl.$^2$ .................................... A45D 7/04
[58] Field of Search ............... 424/71; 132/7; 8/127.51, 10, 10.1

[56] References Cited
UNITED STATES PATENTS

| 2,056,358 | 10/1936 | Malone | 424/71 X |
| 2,169,147 | 8/1939 | Jaeger et al. | 149/2 |
| 2,707,697 | 5/1955 | Wainer | 424/71 X |
| 2,719,104 | 9/1955 | Westerberg | 8/10.1 |
| 2,990,832 | 7/1961 | McDonough et al. | 424/71 X |
| 3,075,821 | 1/1963 | Goldemberg et al. | 8/10 |
| 3,079,213 | 2/1963 | Mendelsohn et al. | 8/115.5 |
| 3,215,605 | 11/1965 | Soloway | 8/10.2 |
| 3,352,624 | 11/1967 | Harding et al. | 8/15 |

*Primary Examiner*—Albert T. Meyers
*Assistant Examiner*—Vera C. Clarke
*Attorney, Agent, or Firm*—William J. Daniel

[57] ABSTRACT

Method for waving and straightening hair by carrying out a metallic chelate reaction in the keratin of the hair by incorporating an alkali metal or ammonium ions or an organic amine into the hair keratin protein, thereafter replacing the alkali metal or ammonium ions or organic amine by metal ions, other than alkali metal ions, said metal ions having a greater atomic weight than that of alkali metal or ammonium ions replaced, said metal ions being derived from aqueous solutions of metal salts other than alkali metals, metal chelate compounds of enzymes, proteins, peptides or amino acids and the lotions and creams as used in the aforesaid method.

8 Claims, No Drawings

WAVING AND STRAIGHTENING HAIR BY PRODUCING METAL CHELATES IN THE KERATIN OF THE HAIR

This application is a continuation of application Ser. No. 100,539, filed Dec. 21, 1970, now abandoned, which in turn is a continuation-in-part of application Ser. No. 596,391, filed Dec. 17, 1966, now abandoned.

This invention relates to a process and also to the hair lotion and hair cream used therein for carrying out hair waving or hair straightening and/or hair coloring.

An object of this invention is to facilitate the process of hair waving or straightening and coloring without heat treatment.

Another object of this invention is to provide a hair lotion and hair cream which can affect waving or straightening and coloring of the hair simultaneously.

A further object of this invention is to provide hair cream that can be used for restoring completely to the original condition hair which has been waved or straightened and/or colored by means of the hair lotion or hair cream of the invention.

These and further objects and advantages of the invention will be clear from the following disclosure.

The aqueous solution used in the process of the invention to wave, straighten or color hair by producing metallic chelate compounds of hair protein keratin comprises one or more solutions selected from solutions of the following substances designated as belonging to group A or group B.

1. Group A consists of an alkaline solution of at least one member selected from the group consisting of organic amines besides hydroxides, carbonate, bicarbonate, oxalate, tartarate and citrate of ammonium or alkali metal on the one hand and nonionic or anionic surface active agents on the other hand.

2. Group B consists of one or more of the solutions of ions of metals other than alkali metals such as alkaline earth metals, aluminum, titanium, chromium, manganese, iron, cobalt, nickel, copper, zinc, zirconium, silver, cadmium, tin, lanthanum, tungsten, platinum, gold, mercury, lead, metal chelate compounds of an enzyme, protein, peptide, or amino acid and in particular of hydrolytic enzymes and more particularly of amylase, protease and lipase.

When the hair is soaked or coated with the aqueous alkaline solution containing therein a dissolved nonionic or anionic surface active agent and calcium oxide and allowed to stand at room temperature, the hair protein keratin produces an insoluble metallic chelate compound containing calcium ions with the resultant waving or straightening of the hair depending on whether the untreated hair was straight or curly. If the hair is then further treated with an aqueous solution of a nonionic or anionic surface active agent and containing metallic ions the atomic weight of which is larger than that of the calcium then the calcium ions of the metallic chelate compound are replaced by the metallic ions having the larger atomic weight. Since different metallic ions impart different colors to the hair, there results the possibility of providing various different hair colors.

The hair protein keratin is constituted of various different amino acids having the following structural formula in which amino acids are successively linked one to the other as follows:

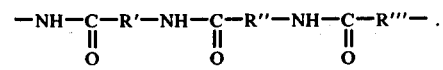

When the hair has swelled as a result of having been soaked in the alkaline solution, it reacts with the ions of sodium, potassium, lithium, ammonium and the like. In the case of sodium, it is presumed that a substance having the following structural formula is obtained.

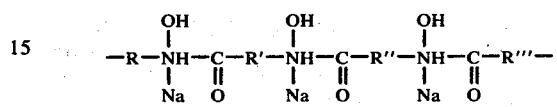

After the hair has been wound up on a roller and soaked in the alkaline solution, it is then soaked in the liquid containing the metal ions, the atomic weight of which is greater than that of the alkali metal. The alkali metal ions of smaller atomic weight which are combined with the hair proteins are thusly replaced by the metal ions having the greater atomic weight to form hair protein chelate compounds of ions of the metals having the larger atomic weight with the resultant waving or straightening of the hair depending on the nature of the untreated hair and in addition the hair is colored.

The products which are formed in the above process can be expressed by the following structural formula.

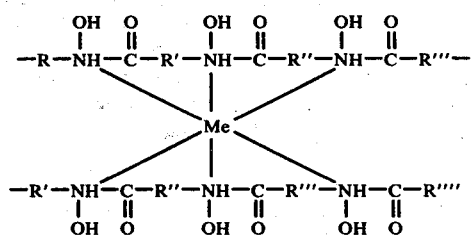

On dehydration of the above, a product having the following structural formula is obtained.

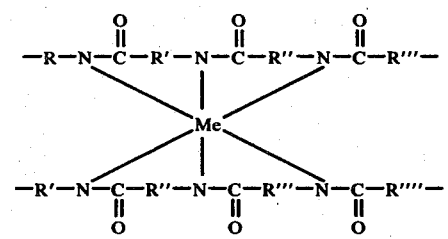

The waving or straightening and coloring of the hair are effected in this condition, the hair evidencing different colors in dependence on the metallic ions which have been used.

The extent to which the hair is artificially curled may be classified into the following five categories.

| | |
|---|---|
| Straight hair | 1 |
| Slight hair wave | 2 |
| Medium hair wave | 3 |
| Strong hair wave | 4 |

| | |
|---|---|
| Very strong hair wave | 5 |

When the artificially curled hair is immersed in warm water, the treated hair tends to revert to its original straight condition. The degree of this reversion is influenced by various factors, such as the time of immersion and water temperature. In order to express the relationship of the degree of reversion to time (minutes) and water temperature (°C), the following method has been adopted.

For instance, if hair which has been waved to the degree of 5, i.e., very strong waves, is soaked in warm water at 40°C for one minute, and is restored to its original straight condition, this is expressed by the value 40151, where 40 indicates 40°C, 1 indicates 1 minute and 51 indicates that the degree of hair waving has been changed from 5 to 1.

If hair which has been waved to the degree of 5, after having been kept in warm water at 40°C for 30 minutes still retains the same degree of wave, then the value is expressed by the numeral 403055.

Permanent waving by means of simple heating techniques may be denoted by the numerical value 40151 and permanent waving by means of chemicals by the value 403055. If artificially straightened natural curl is soaked in warm water at 40°C for 30 minutes and still retains its straightness, then this condition is expressed by the value 403011.

When hair is wound up on a curling roller and soaked for 10 minutes at 50°C in a solution containing 0.25% sodium hydroxide, rinsed in water, soaked again in a different metal ion solution at 50°C for 10 minutes, following which it is washed in water, air dried, taken off from the roller and dipped in water at 40°C for 1 minute and placed on a filter paper for evaluation the following results are obtained.

| Alkali treatment | Metal ions used for substitution | Degree of reversion |
|---|---|---|
| − | − | 40151 |
| + | − | 40151 |
| − | + | 40151 |
| + | aluminum | 40153 |
| + | magnesium | 40153 |
| + | cadmium | 40153 |
| + | zinc | 40154 |
| + | strontium | 40154 |
| + | cobalt | 40155 |
| + | tin | 40155 |
| + | manganese | 40155 |
| + | iron | 40155 |
| + | chromium | 40155 |
| + | silver | 40155 |
| + | gold | 40155 |
| + | platinum | 40155 |
| + | nickel | 40155 |
| + | titanium | 40155 |
| + | copper | 40154 |
| + | zirconium | 40155 |
| + | lanthanum | 40155 |
| + | tungsten | 40154 |
| + | lead | 40155 |
| + | mercury | 40155 |

The source of the metal ions used in the substitution are derived from the corresponding metal chlorides, sulfates, nitrates and acetates. This result has also revealed that the hair can be waved or straightened and colored if it is treated with a solution containing at least one metal ion having a greater atomic weight than does the alkali metal ion, after having been soaked in or coated with an alkaline solution. In case the hair to be treated is white or has very little color, it is tinted with a different color according to the kind of metal ion used in the waving or straightening. The stronger the hair wave, the darker the hair color and vice versa as can be seen from the following table.

| Metal ion | Hair color | Degree of hair waving |
|---|---|---|
| − | original color | − |
| tin | original color | strong |
| zinc | original color | strong |
| cadmium | light yellow | fairly strong |
| strontium | yellow | strong |
| manganese | yellowish brown | strong |
| iron | yellowish brown | strong |
| cobalt | blond | strong |
| nickel | grey | strong |
| chromium | blue | strong |
| silver | dark purple | strong |
| gold | purple | strong |
| platinum | golden | strong |
| chromium and iron mixed | light blond | strong |
| chromium and cobalt mixed | dark brown | strong |
| chromium, iron and cobalt mixed | brownish blond | strong |
| copper | green | strong |

The following table sets out the results which have been obtained by soaking, in warm water (40°C) for 1 minute, cut hair that has been curled by winding the same on a curling roller and then soaking it in or coating it with a solution of sodium hydroxide followed by leaving the hair for 10 minutes in a solution of 3% iron chloride at different temperatures.

| Concentration of sodium hydroxide (%) | Temperature of treatment (°C) Solution of sodium hydroxide | Temperature of treatment (°C) Solution of iron chloride | Degree of reversion |
|---|---|---|---|
| 0.1 | 50 | 50 | 40151 |
| 0.15 | 50 | 50 | 40152 |
| 0.2 | 50 | 50 | 40152 |
| 0.25 | 50 | 50 | 40555 |
| " | 50 | 40 | 40554 |
| " | 40 | 40 | 40152 |
| " | 30 | 40 | 40151 |
| " | 20 | 40 | 40151 |
| 0.3 | 50 | 50 | 40555 |
| 0.3 | 50 | 40 | 40554 |
| " | 40 | 50 | 40553 |
| " | 40 | 40 | 40552 |
| 0.4 | 20–30 | 20–30 | 40151 |
| 0.5 | 20–30 | 20–30 | 40151 |
| 1.0 | 20–30 | 20–30 | 40151 |

From the above, it can be seen that in order to complete the chemical reaction, a quantity of metal ions sufficient to replace the alkali metal ions is necessary and that the temperature used for the treatment must be raised to 50°C.

When cut hair is curled by winding it up on a curling roller and soaking it in an alkaline solution and then further soaked in 3% iron chloride solution for 5 minutes, following which it is soaked again in warm water (40°C) for 5 minutes to allow for reversion, the following relationship between the pH of the solution and the degree of reversion is observed.

| Type of alkaline solution | pH | Degree of reversion |
|---|---|---|
| sodium hydroxide (0.2–1%) | 12.6–13.0 | 40555 |
| calcium hydroxide (0.1%) | 10.8 | 40551 |
| beryllium hydroxide (0.2–2%) | 12.6 | 40555 |
| sodium silicate (¼ mol) | 12.0 | 40555 |
| sodium tertiary phosphate (or potassium) (¼ mol) | 12.0 | 40555 |
| sodium carbonate (¼ mol) | 11.5 | 40555 |
| sodium borate (¼ mol) | 9.0 | 40553 |
| ammonium carbonate (¼ mol) | 8.0 | 40552 |
| sodium acetate (¼ mol) | 8.5 | 40552 |
| sodium lactate (¼ mol) | 8.5 | 40552 |
| sodium citrate (¼ mol) | 8.0 | 40552 |
| disodium hydrogen phosphate (or dipotassium) (¼ mol) | 8.9 | 40551 |
| sodium bicarbonate (¼ mol) | 8.1 | 40551 |
| mixture of sodium succinate and sodium silicate | 10.2 | 40554 |
| mixture of sodium succinate and sodium carbonate | 10.5 | 40554 |
| sodium hydroxide again after being treated by sodium carbonate | 11.5–10.8 | 40555 |

Therefore, it can be seen that as alkaline solution, any type of alkaline salt solution other than a sodium hydroxide solution may be used.

It has become clear that when the hair is coated with a solution of sodium hydroxide and kept at a temperature of 50°C for 10 minutes, the quantity of alkali in the liquid remaining on the hair is reduced to an extremely low level due to the fact that alkali ions are consumed by the combination thereof with the hair protein. In case of an alkaline solution having a concentration of 0.3–0.7%, the hair is waved to a low degree, but in the case of a solution having a concentration of 2–4% it is waved to a high degree. If the hair is coated with a 0.7% solution and the excess liquid removed by means of paper, gauze or the like, and the hair coated again with the same 0.7% solution, the hair waving is twice as strong. Therefore, the repeated coating with relatively dilute alkaline solutions makes it unnecessary to use a concentrated solution.

It has been found that if the hair is treated by means of a 0.1–2% nonionic surface active agent such as polyoxyethylene monostearate, polyoxyethylene monolaurate, polyoxyethylene monooleate, polyoxyethylene lauryl ether, polyoxyethylene cetyl ether, polyoxyethylene lauryl phenol ether, polyoxyethylene cetyl phenol ether, polyoxyethylene oleyl phenol ether, polyoxyethylene cetyl phenol ether, sorbitan monolaurate, sorbitan monopalmitate, sorbitan monostearate, sorbitan monooleate, polyoxyethylene sorbitan monolaurate, polyoxyethylene sorbitan monopalmitate, polyoxyethylene sorbitan monostearate, or alkylol amide or an 0.1–2% anionic surface active agent, namely stearyl sulfate sodium ester, stearyl sulfate diethanolamine ester, stearyl sulfate triethanolamine ester, lauryl sulfate sodium ester, lauryl sulfate diethanolamine ester, lauryl sulfate triethanolamine ester, oleyl sulfate sodium ester, oleyl sulfate diethanolamine ester, oleyl sulfate triethanolamine ester, cetyl sulfate sodium ester, cetyl sulfate diethanolamine ester or cetyl sulfate triethanolamine ester, we can produce hair-waving and hair-coloring without applying heat, i.e., it has been found that hair can be waved and colored at room temperature with safety and with ease.

The number of moles of ethyleneoxide in the above compound is from 5 to 20. The number of carbon atoms in the alkyl group of the above compounds ranges from 12 to 18.

This invention is based on the above-mentioned facts. If the hair is soaked in or coated with an alkaline solution, the keratin of the hair forms chelate compounds with the alkali ions. Hair lotion I consists of an alkaline solution made of a mixture of 0.2 – 4% solution of alkali hydroxide, a 1 – 8% solution of sodium carbonate, or sodium bicarbonate, or 2 – 8% solution of organic amine such as mono-, di-, tri- ethanolamine and an aqueous solution containing 0.1 – 2% nonionic or anionic surface active agent. As a supplement to the above solution, a mixture of 2 – 5% calcium oxide and 0.1 – 2% solution of a surface active agent is used as required. Hair lotion II consists of a solution of 0.1 – 2% nonionic or anionic surface active agent in which there is dissolved 0.1 – 5% of various aqueous soluble metallic salts other than alkali metal salts. Thus the hair waving or hair straightening and also the hair coloring are effected by substituting other metal ions for the alkali metal ions of the chelate compounds of the hair protein keratin by means of hair lotions I and II. In this process, heat is not applied. As the soluble metallic salt, there are used the chlorides, nitrates, sulfates or acetates of such metals as magnesium, aluminum, calcium, titanium, chromium, manganese, iron, cobalt, nickel, copper, zinc, strontium, zirconium, silver, cadmium, tin, barium, lanthanum, tungsten, platinum, gold, mercury, lead, or their mixtures.

In order to restore the hair which has been waved, straightened or colored with the hair lotions I and II to its original color, hair lotion III is used. This lotion III consists of an aqueous solution containing 0.1 – 2% of a nonionic or anionic surface active agent mixed with 0.5 – 5% of an aqueous salt solution of ethylenediaminetetraacetic acid or 8-hydroxyquinoline. The ethylenediaminetetraacetic acid is preferably used in the form of its di-, tri-, or tetra-sodium salt.

Depending on the circumstances, a suitable quantity of perfume is added to the hair lotions I, II and III. It is also possible to provide hair creams as substitutes for the hair lotions I, II and III by adding to these lotions a suitable amount of methyl cellulose, fluid paraffin, lanolin, wax, polyvinylpyrrolidone or the like. The methyl cellulose preferably has a molecular weight of 100,000 to 200,000, and the polyvinylpyrrolidone preferably has a molecular weight of 30,000 to 50,000.

The following is submitted in order to illustrate in further detail, the process of treating the hair by means of hair lotions of this invention.

The hair is wound around a curling roller or straightened from the curled condition by coating the same with hair lotion I by brush application and is kept in this condition at room temperature for 10 minutes. Depending on the circumstances, the liquid remaining on the hair is removed by cotton, cloth or paper, and the hair then coated again with hair lotion I or the supplementary solution and allowed to remain at room temperature for 10 minutes. The hair is then further coated with hair solution II and left at room temperature for 10 minutes.

The hair is thereafter removed from the roller, washed in water, dried with a towel, air dried, coated with oil or cosmetic and styled by combing. Male hair can be waved and styled without using any oil, wax or the like. When coloring is desired along with the waving or straightening of white or grey hair, different colors may be obtained by selecting different types of hair lotion II. If two or three kinds of hair lotion II containing different metal ions are applied alternately interesting vari-colored and frosted effects may be obtained in addition to the waving or straightening. The hair waved or straightened and colored by means of this procedure can be restored to its original condition without suffering any deterioration, if rinsed in hair lotion III.

Further, this invention comprises a single step process for waving or straightening hair by using a mixture of hair lotion I and the abovementioned supplementary solution instead of using the two separately as previously described. The addition of calcium oxide produces calcium hydroxide through its reaction with water. Since the solubility of calcium hydroxide is as low as 0.12% in the water the production of calcium hydroxide is limited to the extent that it can be dissolved. During this process, the insoluble metallic chelate compounds are formed with the hair protein, the alkali metal ions being replaced to produce in this case the calcium chelate compounds of hair protein.

Calcium ions in the hair lotion are consumed and calcium oxide is gradually dissolved in the liquid to supplement the withdrawn calcium ions. Calcium ions produce chelate compounds of calcium by substituting calcium ions for the alkali metal ions in the chelate compounds of the hair protein. The alkali metal ions thus released reacted with further hair protein to form new chelate compounds. The hair is thus waved or straightened through the repetition of this reaction. In this sense, the presence of calcium oxide or other soluble calcium compounds is required. Therefore, due to the requirement for soluble calcium ions, the hair lotion of the invention has to be shaken before being used.

Where a carbonate, bicarbonate, oxalate, tartrate, or citrate of an alkali metal or ammonium is used as a substitute for the alkali hydroxide, the calcium oxide that is also present is converted into calcium hydroxide which reacts with the salts above mentioned to precipitate insoluble calcium carbonate, calcium bicarbonate, calcium oxalate, calcium tartrate or calcium citrate respectively. Thus hydroxides of alkali metals or ammonium are obtained and the result is the same as if the hydroxide of the alkali metal or ammonium were used from the beginning.

Furthermore, by producing a metallic chelate compound which is soluble in alkaline solution by mixing a solution of a surface active agent (nonionic or anionic) and an enzyme in large units, a protein, a peptide or an amino acid and a solution containing a water soluble metal salt and adjusting the hydrogen ion concentration of a resulting mixture to a pH of from 7 – 12, a simple process, using only one kind of mixture in either lotion form or in cream form for hair waving or hair straightening or coloring is obtained.

In order to produce chelate compounds of iron, nickel or the like in hair protein keratin, first a chelate compound of an enzyme or protein with iron, nickel, cobalt or chromium is prepared from the solution of soluble metallic salt such as iron chloride, nickel sulfate, cobalt chloride and chromium sulfate and thereafter the chelate compounds are used with the alkaline solution in place of the metallic ion solution of iron, nickel or the like. If an alkali metal hydroxide solution is added to a water soluble metal salt solution such as iron chloride, nickel sulfate, cobalt chloride and chromium sulfate, these metals precipitate in the form of hydroxides and cannot produce metal chelate compounds in the hair. In order to prevent this precipitation a metal chelate compound which is soluble in alkaline solution is produced by mixing a solution of nonionic or anionic surface active agent and an enzyme in large units, protein, peptide, or amino acid and a solution containing a water soluble metal salt, such as iron, nickel, cobalt, chromium or the like and adjusting the hydrogen ion concentration of the resulting mixture to pH 7 – 12 and the hair is treated with the alkali metal hydroxide solution in which are dissolved 2 – 10% of the above metal chelate compounds together with nonionic or anionic surface active agent.

In this process, iron, nickel, cobalt, chromium, aluminum or zinc in solution, can form chelate compounds of iron, nickel, cobalt, chromium, aluminum or zinc in the hair with the hair keratin.

The treatment of the hair with this mixture will bring about the hair waving or hair straightening and hair coloring. That is to say, if the hair is treated with the aqueous solution of nonionic or anionic surface active agent containing in the dissolved condition the metal chelate compounds of protein (such as casein), peptide (such as peptone), amino acid, or enzyme (such as amylase, protease, or lipase), the metal chelate compounds of hair protein are formed which wave or straighten and color the hair. The hair can take on different colors depending upon which soluble metal salt is selected.

The following is given in order to more fully illustrate the invention but is not to be construed as limitative of the scope thereof.

EXAMPLE 1

Hair lotion I consists of an aqueous alkaline solution containing 1% sodium hydroxide and 0.5% by weight polyoxyethylene lauryl ether. Hair lotion II consists of a solution of 0.5% by weight polyoxyethylene lauryl ether in which 0.5% of cobalt chloride dissolved.

The hair, wound around the roller or straightened from the curled condition, is coated with hair lotion I by means of a brush and is kept at room temperature for 10 minutes. Depending on the circumstances, the liquid remaining on the hair is removed with cotton, cloth or paper and the hair coated again with hair lotion I and left at room temperature for 10 minutes, after which the hair is coated with hair lotion II and left at room temperature for 10 minutes.

Then the hair is removed from the roller, washed in water, wiped with a towel, air dried, coated with oil or cosmetic and styled by combing. Male hair can be waved and styled without using oil, wax or the like. In straightening the hair, the hair is combed with a brush and coated with hair lotion I. In the case of long hair, it is wound up on a thick roller and similarly coated with hair lotion I. A cap is placed on the head, the hair in this condition is left at room temperature for 10 minutes and thereafter is treated in the same manner as when it is waved.

The hair that has been waved or straightened can be restored to its original condition by washing the same with hair lotion III consisting of an aqueous solution of 0.5% of polyoxyethylene lauryl phenol ether and 3% trisodiumethylenediaminetetraacetic acid. When coloring is desired together with the waving or straightening of white or grey hair, different kinds of colors may be obtained by selecting different kinds of hair lotions II. If two or three kinds of hair lotions II containing different metal ions are applied alternately, interesting colored and froated effects in addition to waving or straightening may be obtained. The hair which has been waved or straightened and colored by means of said process can be restored to its original condition without suffering any damage if it is rinsed in hair lotion III.

EXAMPLE 2

By adding 5% of methyl cellulose to hair lotion I (prepared as an aqueous solution of 0.5% of polyoxyethylene lauryl ether containing a dissolved 0.5% sodium hydroxide) and to hair lotion II (prepared as an aqueous solution of 0.5% polyoxyethylene lauryl ether containing a dissolved 0.5% of nickel sulfate), creams corresponding to hair lotion I and II respectively, are produced which may be used for hair waving or hair straightening and coloring.

EXAMPLE 3

3 grams of potassium hydroxide and 3 grams of calcium oxide are added to 100 ml of water which is shaken in order to dissolve the calcium hydroxide which is thereby formed and in order to keep the rest of the calcium oxide in suspension so that the entire liquid has a milky appearance. There is dissolved in this liquid 0.5% polyethylene glycol monolaurate to produce a hair lotion, to which a suitable quantity of perfume is added if desired. The process of hair waving with this lotion consists of coating the hair with a small quantity of water, winding it on a roller, then coating it with a hair lotion by means of a brush and leaving it for 15 minutes after which the roller is removed and the hair is washed in warm water. Then the hair is wiped dry with a towel and air dried after which hair oil is applied and the hair styled by combing. Curly hair can easily be straightened by treating with this hair lotion. The hair which has been straightened is colored by coating with a lotion made from an aqueous solution of 1% polyoxyethylene lauryl phenol ether containing 1g strontium nitrate, the metal of which has an atomic weight which is larger than that of calcium. Many different colors can be imparted to the hair according to the type of soluble metal salt used.

EXAMPLE 4

Pulverized calcium oxide is added to an aqueous solution containing 2.5% sodium bicarbonate and 1% lauryl sulfate sodium ester as surface active agent. The resulting solution is a milky suspension. Perfume as well as a coloring pigment is added to the suspension. By the addition of a 5% cream base to this solution, a hair cream is obtained.

EXAMPLE 5

A hair lotion to be used for waving or straightening the hair is obtained by dissolving 2% sodium carbonate and 4% sodium oxalate in an aqueous solution containing 1% lauryl sulfate diethanolamine ester. To this resultant solution, there is introduced calcium oxide and a suitable quantity of perfume and pigment. If the hair is coated with this lotion and held under a cap for 10 to 20 minutes the hair is either straightened or waved.

EXAMPLE 6

2% Casein is dissolved in 100 ml of 0.2% ammonium hydroxide solution containing 0.5% of stearyl sulfate diethanolamine ester and to the resultant solution there is added 1% cobalt chloride. Sodium hydroxide is then added to adjust the pH of the solution to a value of over 7. A hair lotion suitable for waving or straightening and coloring the hair is obtained.

EXAMPLE 7

2% Amylase is dissolved in 100 ml of alkaline solution containing 2% of lauryl sulfate sodium ester and to the resultant solution there is added 1% iron chloride. Sodium hydroxide is used to adjust the pH of the solution to a value of over 7. There results a hair lotion which when mixed with 1.5% polyoxyethylene cetyl phenol ether and a suitable quality of perfume and pigment forms a hair cream to be used for waving, straightening and coloring the hair.

EXAMPLE 8

Hair waving is carried out with a hair lotion comprising a solution containing 5 parts of sodium bicarbonate, 3 parts of triethanolamine and 3 parts of calcium oxide dissolved in 100 parts of water. The hair lotion is applied to the hair. The hair is left at room temperature for 20 minutes after having been partially rolled up on a hair roller, and then the hair is removed from the roller and washed with a shampoo. A beautiful and strong hair wave is obtained.

EXAMPLE 9

Hair straightening is carried out by applying a hair cream by combing to curly or frizzy hair which consists of 4 parts of water glass, 2 parts of sodium bicarbonate, 3 parts of calcium oxide and 0.2 parts of polyethylene glycol monostearate dissolved in 100 parts of water and to which there has been added 5 parts of methyl cellulose. After leaving the lotion on at room temperature for 10 to 20 minutes, the hair is washed with a shampoo. Lustrous and beautifully straight hair is obtained.

EXAMPLE 10

Hair is colored by applying to color-free hair a solution containing 2 parts of sodium hydroxide and 3 parts of monoethanolamine dissolved in 100 parts of water. The hair is left for 15 minutes covered with a vinyl cap and after the cap is removed, an aqueous solution of 5% cobalt chloride and 0.5% of polyoxyethylene lauryl phenol is applied to the hair. The hair is left at room temperature for 10 to 15 minutes and is washed. Blond colored hair is thereby obtained.

EXAMPLE 11

2% Peptone is dissolved in 100 ml of alkaline solution containing 2% of lauryl sulfate triethanolamine ester and to the resultant solution there is added 1% silver nitrate. Sodium hydroxide is then used to adjust the pH of the solution to a value of over 7. There results a hair lotion which when mixed with 1% oleyl sulfate diethanolamine ester and a suitable quantity of perfume and 5% of methyl cellulose forms a hair cream to be used for hair waving, hair straightening and hair coloring.

EXAMPLE 12

Hair waving is carried out with a hair lotion comprising a solution containing 5 parts of sodium bicarbonate, 3 parts of triethanolamine, 2 parts of aluminum sulfate dissolved in 100 parts of water. The hair lotion is applied to the hair. The hair is left at a room temperature for 20 minutes after having been partially rolled up of a hair roller and then hair is removed from the roller and washed with a shampoo. A beautiful and strong hair wave is obtained.

EXAMPLE 13

Hair waving is carried out with a hair lotion comprising a solution containing 5 parts of sodium bicarbonate, 3 parts of triethanolamine, 2 parts of magnesium sulfate dissolved in 100 parts of water. The hair lotion is applied to the hair. The hair is left at a room temperature for 20 minutes after having been partially rolled up of a hair roller and then hair is removed from the roller and washed with a shampoo. A beautiful and strong wave is obtained.

EXAMPLE 14

Hair is colored by applying to color-free hair a solution containing 2 parts of sodium hydroxide and 3 parts of monoethanolamine dissolved in 100 parts of water. The hair is left for 15 minutes covered with vinyl cap and after the cap is removed, an aqueous solution of 2% cobalt chloride and 0.1% chromium alum, and 0.5% of polyoxyethylene lauryl ether is applied to the hair. The hair is left at room temperature for 10–15 minutes and is washed. Blond colored hair is thereby obtained.

EXAMPLE 15

2% of histidine is dissolved in 100 ml of 0.2% potassium hydroxide solution containing 2% of stearyl sulfate diethanolamine ester and to the resultant solution there is added 1% aluminum alum. Potassium hydroxide is then added to adjust the pH of the solution to the value of over 7. A hair lotion suitable for waving or straightening and coloring the hair is obtained.

What is claimed is:

1. A two-stage treatment for curling initially straight hair or straightening initially curly hair, which comprises arranging the hair in one of said curled or straight configurations different from the configuration of the untreated hair, soaking the hair so arranged with a first aqueous solution consisting essentially of 0.2–8% of at least one of a water-soluble organic amine, a water-soluble alkali metal hydroxide, a salt of an alkali metal, ammonium hydroxide or an ammonium salt having a pH of about 8–13 and while said hair is so soaked, soaking the still arranged hair with a second aqueous solution consisting essentially of 0.1–5% of a water-soluble salt of a metal which has an atomic weight heavier than an alkali metal and is adapted to form a chelate complex with hair keratin for a sufficient time to form said chelate complex.

2. The treatment of claim 1 wherein at least one of said solutions also contains an anionic or non-ionic surfactant in the amount of 0.1–2% and said solutions are applied to the hair at about room temperature.

3. The treatment of claim 1 wherein in said first aqueous solution said salt is a carbonate, a bicarboxate, an oxalate, a tartrate or a citrate of said alkali metal or ammonium.

4. The treatment of claim 1 wherein said first solution has a pH of at least 10.

5. A one-stage treatment for curling initially straight hair or straightening initially curly hair, which comprises arranging the hair in one of said curled or straight configurations different from the configuration of the untreated hair, soaking the hair so arranged with an aqueous solution having a pH of about 8–13 consisting essentially of 0.2–8% of at least one of a water-soluble organic amine, a water-soluble alkali metal hydroxide, a salt of an alkali metal, ammonium hydroxide or an ammonium salt, and 0.1–5% of a salt of a metal having an atomic weight heavier than an alkali metal, which salt has significant water-solubility at said pH and releases ions of said metal in aqueous solution, and said metal forming a chelate complex with hair keratin.

6. The treatment of claim 5 wherein said solution also contains 0.1–2% of an anionic or non-ionic surfactant.

7. A one-stage treatment for curling initially straight hair or straightening initially curly hair, which comprises arranging the hair in one of said curled or straight configurations different from the configuration of the untreated hair, soaking the hair so arranged with an aqueous solution consisting essentially of 0.1–2% of an anionic or non-ionic surfactant, 2–10% of a water-soluble chelate, said chelate being of an enzyme, a protein, or an amino acid with a metal which has an atomic weight heavier than an alkali metal and is adapted to form a chelate complex with hair keratin, and at least one of a water-soluble organic amine, an alkali metal hydroxide, a salt of an alkali metal, ammonium hydroxide or an ammonium salt, having a pH of from 7–12, for a time sufficient to form a chelate complex with the hair keratin.

8. The treatment of claim 7 wherein said water-soluble chelate is a chelate of said metal with peptone, casein, amylase, protease, lipase or histidine.

* * * * *